US012673342B1

(12) United States Patent
Hogan et al.

(10) Patent No.: US 12,673,342 B1
(45) **Date of Patent: \*Jul. 7, 2026**

(54) AEROSOL GENERATOR

(71) Applicant: Stamford Devices Limited, Dangan (IE)

(72) Inventors: Brendan Hogan, Gort (IE); Kieran Hyland, Galway (IE); Anthony Redmond, Galway (IE)

(73) Assignee: Stamford Devices Limited, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 19/294,419

(22) Filed: Aug. 8, 2025

Related U.S. Application Data

(63) Continuation of application No. 18/413,487, filed on Jan. 16, 2024, which is a continuation of application
(Continued)

(51) Int. Cl.
*B05B 17/00* (2006.01)
*A61M 11/00* (2006.01)

(52) U.S. Cl.
CPC ........ *B05B 17/0646* (2013.01); *A61M 11/005* (2013.01); *A61M 2205/0294* (2013.01)

(58) Field of Classification Search
CPC ............ B05B 17/0607; B05B 17/0615; B05B 17/063; B05B 17/0638; B05B 17/0646;
(Continued)

(56) References Cited

U.S. PATENT DOCUMENTS 4,976,259 A    12/1990    Higson et al.
5,014,004 A    5/1991    Kreibich et al.
(Continued)

FOREIGN PATENT DOCUMENTS

DE    3533227 A1    4/1986
DE    10122065 A1    12/2002
(Continued)

OTHER PUBLICATIONS

Extended European Search Report dated Dec. 18, 2020 in European Application No. 20207577.6.
(Continued)

*Primary Examiner* — Christopher R Dandridge
(74) *Attorney, Agent, or Firm* — Bookoff McAndrews, PLLC

(57) ABSTRACT

An aerosol generator has a vibratable plate with apertures therein and an annular piezo which causes movement of the vibratable plate. An annular support member supports the piezo and the vibratable plate. A first electrical power conducting pin engages directly with a first, top, surface of the piezo. A second electrical power conducting pin indirectly conducts electrical power to a second surface of the piezo, by contacting an extension tab of the support member, also on its top side. There is a film of cured epoxy adhesive on the tab, providing excellent gripping force between the pin and the support. The aerosol generator avoids need for soldered joints for electrical contact, and the pins are conveniently mounted parallel to each on the on the same lateral and top side of the piezo and support member. The pins may have multi-point tips for particularly effective electrical contact.

20 Claims, 5 Drawing Sheets

Related U.S. Application Data

No. 16/390,750, filed on Apr. 22, 2019, now Pat. No. 11,904,340, which is a continuation of application No. 15/476,242, filed on Mar. 31, 2017, now Pat. No. 10,322,432, which is a continuation of application No. 15/048,358, filed on Feb. 19, 2016, now Pat. No. 10,092,924, which is a continuation of application No. 13/251,924, filed on Oct. 3, 2011, now Pat. No. 9,289,792.

(60) Provisional application No. 61/389,502, filed on Oct. 4, 2010.

(58) Field of Classification Search
CPC .............. A61M 11/001; A61M 11/005; A61M 15/0085
See application file for complete search history.

(56) References Cited

U.S. PATENT DOCUMENTS

| | | | |
|---|---|---|---|
| 5,297,734 A | 3/1994 | Toda | |
| 5,435,282 A | 7/1995 | Haber et al. | |
| 6,085,740 A * | 7/2000 | Ivri | A61M 11/005 |
| | | | 239/102.1 |
| 6,159,056 A | 12/2000 | Boyle | |
| 6,205,999 B1 | 3/2001 | Ivri et al. | |
| 6,296,196 B1 * | 10/2001 | Denen | B05B 17/0684 |
| | | | 239/102.1 |
| 6,530,370 B1 | 3/2003 | Heinonen | |
| 6,539,937 B1 | 4/2003 | Haveri | |
| 6,732,944 B2 | 5/2004 | Litherland et al. | |
| 6,769,626 B1 * | 8/2004 | Haveri | A61M 15/0085 |
| | | | 239/338 |
| 6,978,941 B2 | 12/2005 | Litherland et al. | |
| 7,360,536 B2 | 4/2008 | Patel et al. | |
| 7,891,352 B2 | 2/2011 | Gallem et al. | |
| 7,954,730 B2 | 6/2011 | Ng | |
| 8,333,187 B2 | 12/2012 | Gallem et al. | |
| 9,016,272 B2 | 4/2015 | Gallem et al. | |
| 9,027,548 B2 | 5/2015 | Borgschulte et al. | |
| 9,289,792 B2 | 3/2016 | Hogan et al. | |
| 9,339,838 B2 | 5/2016 | Moran et al. | |
| 10,399,109 B2 | 9/2019 | Hogan et al. | |
| 10,695,787 B2 | 6/2020 | Hogan et al. | |
| 11,446,695 B2 * | 9/2022 | Hogan | A61M 11/001 |
| 2003/0102877 A1 | 6/2003 | Souza et al. | |
| 2003/0196660 A1 | 10/2003 | Haveri | |
| 2003/0218077 A1 | 11/2003 | Boticki et al. | |
| 2004/0050947 A1 | 3/2004 | Power et al. | |
| 2005/0056274 A1 | 3/2005 | Kunschir | |
| 2005/0253605 A1 | 11/2005 | Lee | |
| 2006/0207591 A1 | 9/2006 | Gallem et al. | |
| 2006/0243820 A1 | 11/2006 | Ng | |
| 2007/0044792 A1 | 3/2007 | Ivri | |
| 2007/0267010 A1 | 11/2007 | Fink et al. | |
| 2008/0006264 A1 * | 1/2008 | Gallem | A61M 15/0021 |
| | | | 128/200.14 |
| 2008/0061809 A1 | 3/2008 | Lee et al. | |
| 2008/0308096 A1 * | 12/2008 | Borgschulte | A61M 11/005 |
| | | | 128/200.14 |
| 2009/0235925 A1 | 9/2009 | Power et al. | |
| 2009/0261851 A1 | 10/2009 | Zhou et al. | |
| 2010/0213274 A1 | 8/2010 | Yu et al. | |
| 2010/0319685 A1 | 12/2010 | Yu | |
| 2011/0230820 A1 * | 9/2011 | Lillis | A61M 13/00 |
| | | | 604/24 |
| 2012/0111970 A1 | 5/2012 | Hogan et al. | |
| 2012/0167877 A1 | 7/2012 | Pumm et al. | |
| 2015/0034075 A1 | 2/2015 | Gallem et al. | |

FOREIGN PATENT DOCUMENTS

| | | |
|---|---|---|
| DE | 102005006374 B3 | 7/2006 |
| DE | 102005006375 A1 | 8/2006 |
| DE | 102009026636 A1 | 12/2010 |
| EP | 1332006 A1 | 8/2003 |
| EP | 1875936 A1 | 1/2008 |
| EP | 101627917 | 5/2010 |
| WO | 0119437 A1 | 3/2001 |
| WO | 0176762 A2 | 10/2001 |
| WO | 0236269 A1 | 5/2002 |
| WO | 02087773 A1 | 11/2002 |
| WO | 2011061479 A1 | 5/2011 |
| WO | 2011083379 A1 | 7/2011 |
| WO | 2011141475 A1 | 11/2011 |

OTHER PUBLICATIONS

Extended European Search Report for EP 17 15 5020, dated May 19, 2017, 7 pages.
International Search Report for corresponding PCT/IE2011/000054 dated Feb. 162012.
International Search Report for PCT/IE2011/000054 dated Feb. 16, 2012.
Notice of Opposition to European Patent No. EP2624967B1. Jun. 22, 2016, 5 pages.
Written Opinion for corresponding PCT/IE2011/000054 dated Feb. 162012.
Written Opinion for PCT/IE2011/000054 dated Feb. 16, 2012.

* cited by examiner

AEROSOL GENERATOR

INTRODUCTION

This invention relates to aerosol generators.

Aerosol generators of the type comprising a vibratable apertured membrane, a vibration generator such as a piezo element, and a support are known. An aerosol generator of this type is illustrated in FIGS. 1 and 2. A membrane 201 is supported by a metal washer 203 on top of which there is an annular piezo 202. When the piezo 202 is electrically excited it moves in a radial direction as shown by the arrow A. This causes the apertured plate or membrane to move in a vertical direction as shown by the arrow B. This, in turn, causes liquid on the apertured plate to pass through the holes in the membrane 1 and thus delivering a fine mist of aerosol to the underside of the membrane 1.

To electrically excite the piezo 202, electrical power must be conducted to it and connected on each side. Traditionally, this is done by soldering wires to the conductive surfaces of the vibration generator. The other ends of the wires are soldered to conductive electrical pins which are held in a nebulizer housing to receive the female end of a detachable cable. This arrangement is illustrated in FIG. 2, from which it will be seen that there are four connections 205, 206, 207, and 208.

This method of connection suffers from the disadvantage that the four connections must be soldered. Soldering is a labour-intensive operation and does not lend itself to automation.

U.S. Pat. No. 5,435,282 (Haber) also describes a nebulizer. In this case the membrane is supported by a housing having a downwardly-depending skirt. The piezo is a discrete element on one side of the housing. A contact pin contacts the top surface of the piezo and another two pins contact the underside of the housing.

The invention is directed towards providing an improved aerosol generator, in which soldered contacts are minimized or eliminated while also achieving a simple arrangement of parts.

SUMMARY OF THE INVENTION

According to the invention, there is provided an aerosol generator comprising:

a vibratable member having apertures therein;

a vibration generating element, whereby excitation of the vibration generating element causes movement of the vibratable member;

a support member, the vibration generating element and the vibratable member being mounted to the support member;

a first electrical power conducting pin which engages with a first surface of the vibration generating element;

a second electrical power conducting pin for conducting electrical power to a second surface of the vibration generating element;

wherein the vibration generating element and the support member are annular, and wherein the second surface of the vibration generating element is mounted to the support member, and the second conducting pin engages with the support member.

In one embodiment, the vibration generating element is mounted to the support member by means of an electrically conductive adhesive.

In one embodiment, at least one electrical conducting pin comprises a multipoint contact region.

In one embodiment, there is in the range of 7 to 14 tips in said multipoint contact region.

In one embodiment, the support member includes a substrate and a film and the second conducting pin contacts said film.

In one embodiment, the film is cured adhesive.

In one embodiment, the adhesive comprises an epoxy.

In one embodiment, the film has a hardness in the range of 70 to 85 Shore D.

In one embodiment, the film has a tensile modulus in the range of 2,000-7,000 MPa.

In one embodiment, the vibration generating element is secured to the support member by an adhesive, and the film is of the same material as said adhesive.

In one embodiment, the second conducting pin contacts an extension tab of the support member.

In one embodiment, the second conducting pin contacts an extension tab of the support member and said film is in the form of a discrete pad on the extension tab.

In one embodiment, said adhesive is spaced apart from adhesive under the vibration generating element.

In one embodiment, said substrate comprises a steel washer.

In one embodiment, each of the conducting pins comprises a spring pin.

In one embodiment, the first and second conducting pins are identical.

In one embodiment, the pins comprise a barrel and a plunger which is biased by a spring housed in the barrel.

In one embodiment, the spring contact force exerted is in the range of 1.3N to 3 N.

In one embodiment, the plunger of the pin is of a material with a low electrical resistivity.

In one embodiment, the material of the plunger is selected from Beryllium Copper alloy, Nickel, Copper Zinc alloy, or Stainless Steel.

In one embodiment, an interfacial contact surface of at least one pin has a coating thereon to prevent oxidation of the interfacial surfaces.

In one embodiment, the coating comprises a metallic coating.

In one embodiment, the coating comprises an undercoating and an outer coating.

In one embodiment, the undercoating comprises nickel or silver.

In one embodiment, the outer coating comprises gold or nickel.

In one embodiment, the pins are substantially parallel to each other, extending on the same side of the vibration generating element and the support member.

In one embodiment, the pins are offset laterally on one side of the support member and the vibration generating element.

In one embodiment, the generator further comprises a retainer supporting an assembly of the support member, the vibration generation element, and the vibratable member; wherein the retainer engages an underside of the support member via an annular seal and engages a top surface of the support member via a top counter-balancing annular seal.

In one embodiment, the top annular seal is adjacent the edge of the vibratable member and has a smaller radial dimension then the bottom annular seal.

In one embodiment, the bottom annular seal contacts the support member at a location underneath the vibration generating element, and the top annular seal contacts the support member laterally inside of the vibration generating element.

According to another aspect, the invention provides an aerosol generator comprising:

a vibratable member having apertures therein;

a vibration generating element, whereby excitation of the vibration generating element causes movement of the vibratable member;

a support member, the vibration generating element and the vibratable member being mounted to the support member;

a first electrical power conducting pin which engages with a first surface of the vibration generating element;

a second electrical power conducting pin for conducting electrical power to a second surface of the vibration generating element;

wherein the vibration generating element and the support member are annular, and wherein the second surface of the vibration generating element is mounted to the support member, and the second conducting pin engages with the support member, and wherein at least one electrical conducting pin comprises a multipoint contact region.

BRIEF DESCRIPTION OF THE DRAWINGS

The invention will be more clearly understood from the following description of an embodiment thereof, given by way of example only, with reference to the accompanying drawings, in which.

DETAILED DESCRIPTION

Figures 1A, 1B, 2:
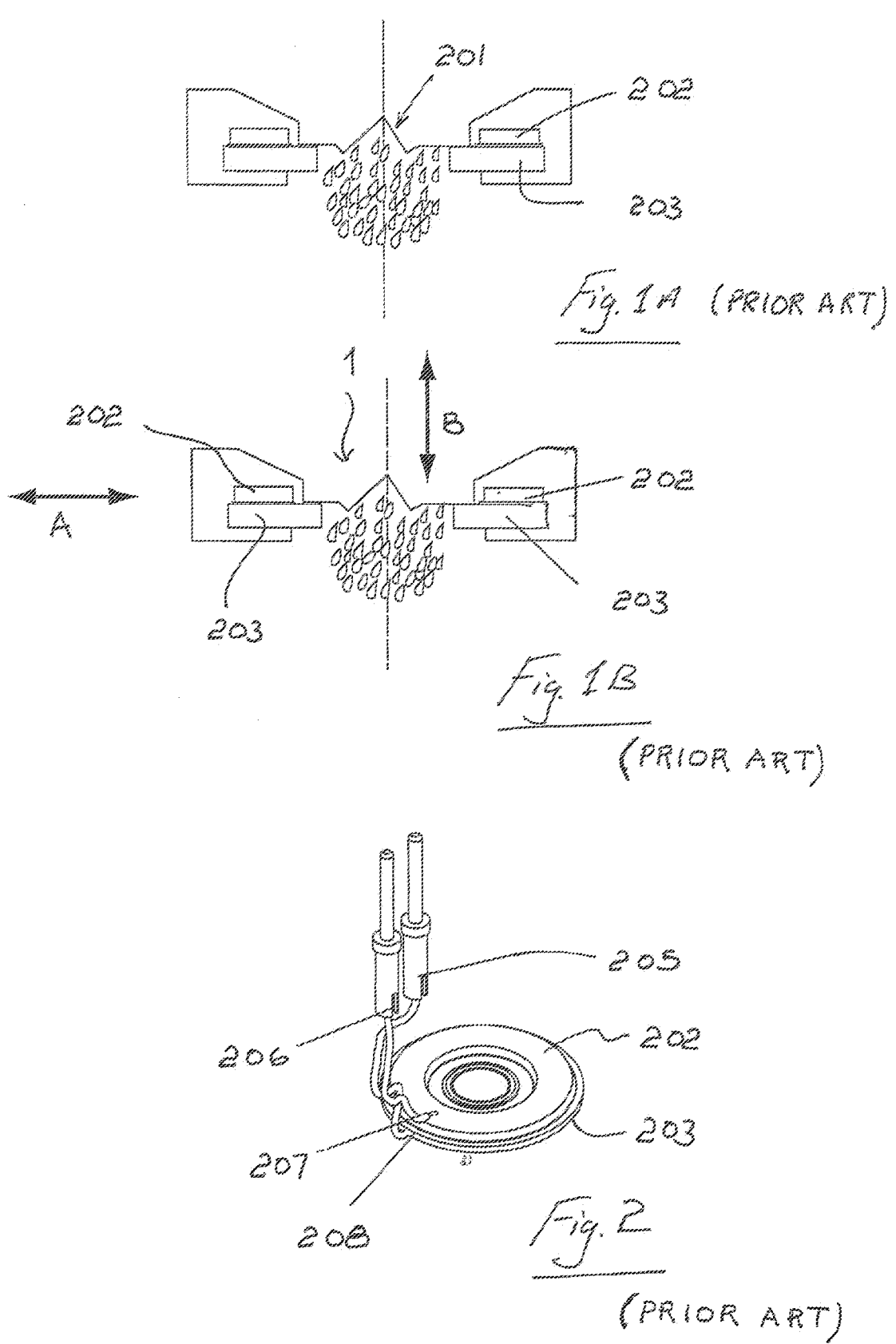
FIGS. 1A and 1B are diagrammatic cross sectional views of a prior art aerosol generator.
FIG. 2 is a perspective view of the connection of the aerosol generator of FIGS. 1A and 1 B to conductive electrical pins.
Figure 3:
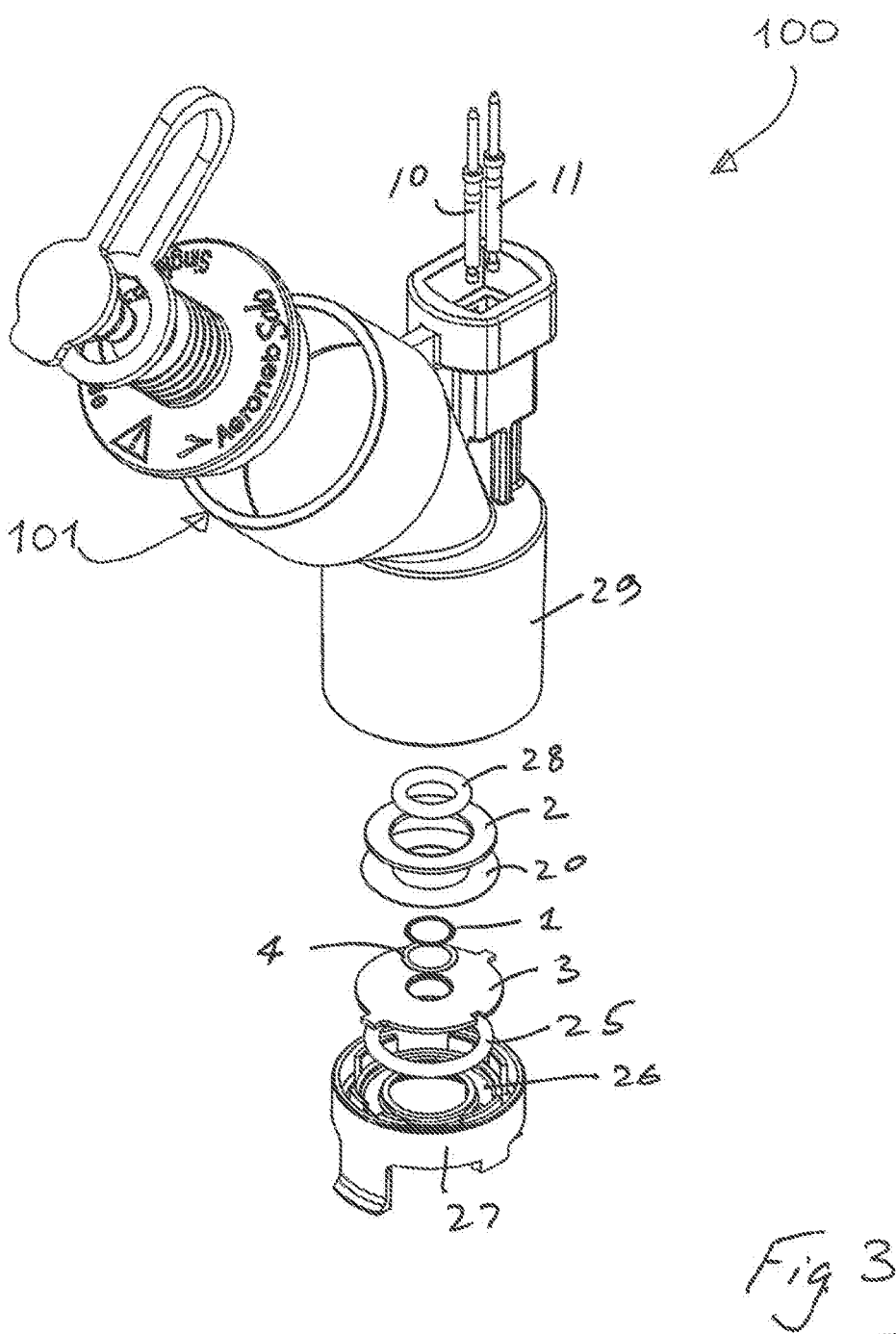
FIG. 3 is an exploded perspective view of an aerosol generator according to the invention.

Referring to FIGS. 3 to 6 of the drawings there is illustrated an aerosol generator 100 according to the invention. The aerosol generator comprises a vibratable member such as a vibratable aperture plate 1, a vibration generator 2, and a support washer 3. The vibration generator 2 in this case comprises an annular piezoelectric element ("piezo") 2 having a first or upper surface and a second or lower surface. The piezo 2 is supported by the washer 3. The aperture plate 1 is supported by the support washer 3. A braze ring 4 is also provided.

In use, liquid to be aerosolised is received at a first upper surface of the aperture plate 1 and the piezo 2 is activated. Aerosolised liquid is generated at the second or lower surface of the aperture plate 1 by ejecting droplets of liquid upon activation of the piezo 2. The apertures in the aperture plate 1 are sized to aerosolise the liquid such that the majority of the droplets have a size of less than 6 micrometers.

The vibratable member could be non-planar, and may be dome-shaped in geometry.

Figures 4, 5, 6:
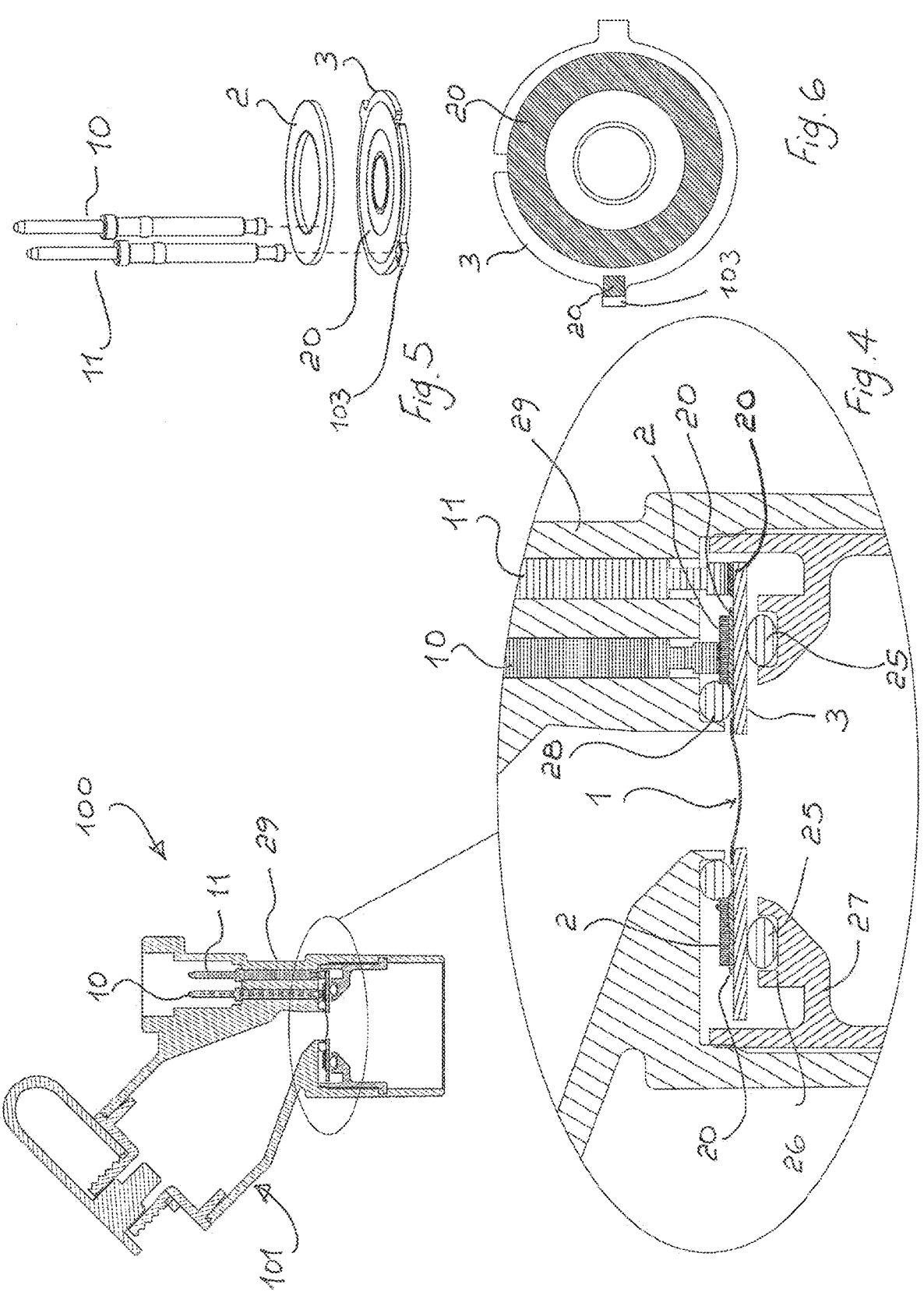
FIG. 4 is a cross sectional view of an aerosol generator according to the invention, including an enlarged view illustrating the core in more detail.
FIG. 5 is a perspective view showing how pins make solderless contact to drive the piezo.
FIG. 6 shows conductive adhesive application on a support washer.

Electrical power is supplied to the piezo 2 in this case by a first conducting pin 10 and a second conducting pin 11. The first conducting pin 10 is in direct contact with the upper surface of the piezo 2. The second conducting pin 11 is in electrical contact with the upper surface of the support washer 3 via conductive adhesive 20 on a tab 103 of the support washer 3. The washer 3 and the conductive adhesive 20 are in turn is in electrical contact with the lower surface of the piezo 2. This arrangement is best illustrated in FIGS. 4 to 6.

The support washer 3 in turn engages against a lower O-ring 25 which is housed in a groove 26 of a support housing 27. The support washer 3 also engages against an upper O-ring 28 in the upper part 29 of the main housing. The washer 3 is sandwiched between the upper O ring 28 and the lower 0 ring 25. This subassembly is in turn sandwiched between the upper housing 29 and the lower retainer clip 27. The arrangement of the lower retaining clip 27 provided uniform support around the support member 3, counter-balanced by the support forces applied via the O-ring 28 and the pins 10 and 11. This helps to achieve consistent operation of the aerosol generator 100, with reduced risk of fatigue in the seal between the plate 1 and the support washer 2, and a predictable plate vibration response to the applied electrical drive.

To accommodate automation low-cost manufacture and consequently greater manufacturing capacities to supply higher volume market demands, both spring pins 10, 11 are the same and are placed in the same direction of orientation.

By attaching the piezo 2 to the support washer 3 using an electrically conductive means, the second spring pin 11 provides electrical communication to the underside of the piezo 2 through the top surface of the washer 3. The first spring pin 10 provides electrical conduction through the top surface of the piezo 2.

In the invention electrical spring pins 10, 11 are used to connect directly between the female end of a detachable cable and the electrical surfaces of the piezoelectric generator 2. No soldering is required and the use of such pins facilitates assembly by automatic means.

To facilitate greater capacities, and to supply higher volume market demands the electrically conductive liquid adhesive 20 is used to attach the underside of the piezo 2 to the washer 3. This is applied by automatic means. The viscosity, rheology, application rate, bead thickness, pressure of support washer/piezo contact are optimised to facilitate application of the conductive liquid adhesive by automatic means, both in the annular pattern and as a pad on the tab 103. Such adhesives may be cured at normal temperature or may require exposure to higher predetermined temperatures for a preset period of time to form a strong bonding attachment. The optimum bonding attachment is achieved when the adhesive is cured to provide optimum strength condition. Epoxies are particularly suited for this application and more particularly those with tensile moduli in the range of 300 to 10,000 MPa and more typically in the range of 2,000-7,000 MPa. Such materials have resistances in the order of 1 milliohm/cm2, but could be higher up to 100 milliohm/cm2. Optimum mechanical properties are achieved when such adhesives are cured in the ranges of 3 minutes at 175 degrees centigrade to 240 minutes at 100 degrees centigrade. Typical hardness are in the range of 70-85 Shore D (ASTM D2240).

The piezo 2 may alternatively be attached to the washer 3 by means of soldering by automatic means to provide an electrically conductive path between the top of the washer and the bottom of the piezo 2.

Typically the piezo 2, when electrically excited, vibrates at approximately, 134 KHz. This presents several problems.

Using the spring pins 10 and 11, the interfacial electrical connection between the spring contact surface and the surface of the support washer 3 and the piezo 2, will be in pressure contact rather than mechanically connected together as with soldered joints. To ensure good electrical contact with spring pressure pins while the assembly vibrates at 134 KHz, to aerosolise medication in a corrosive ventilation circuit environment, the interfacial connection between the spring pin contact area and the surface of the washer and piezo are critical. Nebulisers incorporating the aerosol generator of the invention must be able to perform in a wide range of modes of use. Such nebulizers are often used intermittently over a 28 day period or can be used continuously for up to 7 days.

A number of undesirable mechanisms can occur such as oxidisation, corrosion mechanism, galvanic corrosion, mechanical vibrations, fretting wear to cause loss of electrical contact at the interface.

Figures 7, 8, 9:
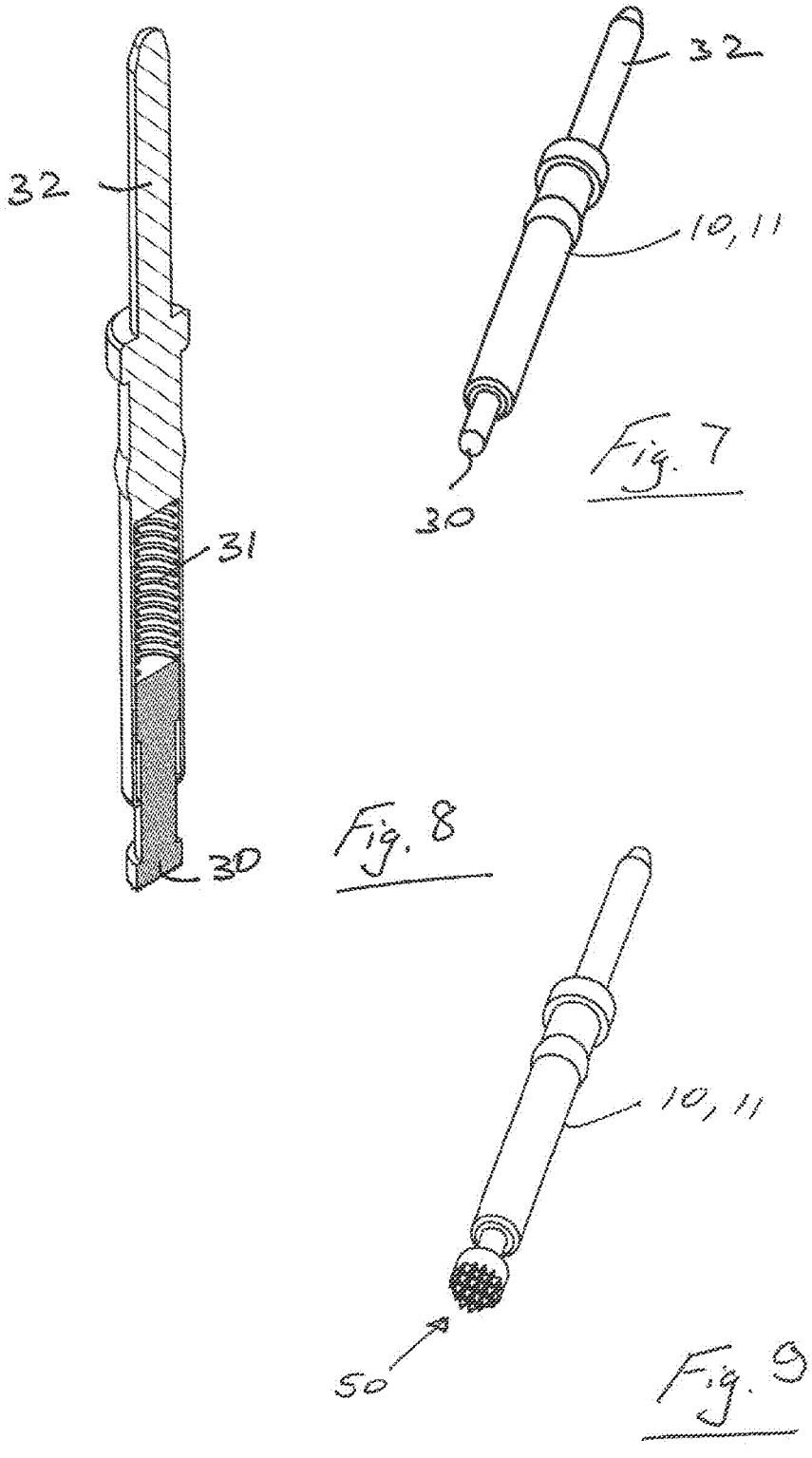
FIG. 7 is a perspective view of a spring pin.
FIG. 8 is a cross sectional view of the pin of FIG. 7.
FIG. 9 is a perspective view of an alternative spring pin according to the invention.

Referring particularly to FIG. 8, each pin 10, 11 comprises a plunger 30, a spring 31 and a barrel 32.

The spring contact force exerted by the spring pin is approximately between 1.3 and 3 Newtons which helps to reduce fretting wear as there is less pin bounce on the surface.

Choosing pin materials of a low electrical resistivity such as Beryllium Copper alloy (BeCu), Nickel (Ni), or Copper Zinc alloy (CuZn) and stainless steel (SS 303) contributes to increased electrical conductivity. Barrel materials such as copper, brass and bronze alloys exhibit good electrical conductivity as well as good corrosion resistance and mechanical strength and are suitable for this application.

Metallic coatings to prevent oxidisation of the interfacial surfaces such as Gold (Ag) over Nickel (Ni), also contribute to increased electrical conductivity. Coatings of 1-3 microns of gold over 3 microns of Nickel undercoat are particularly suitable. Spring parent materials can consist of Music Wire (ASTM A 228) and 304 Stainless Steel. Metallic coatings such as 0.05 microns of Gold over a 0.05 micron Nickel undercoat are especially suitable 'Constriction' of the electrical current at the electrical interface increases the contact electrical resistance and can cause an undesirable rise in temperature. The total effective area of electrical contact needs to be made as large as possible to help create and maintain acceptable quality of electrical connection.

A conventional semi-hemispherical pin head has the disadvantage of not being able to expose new effective contacting surfaces.

Figures 10A, 10B, 10C, 10D, 10E:
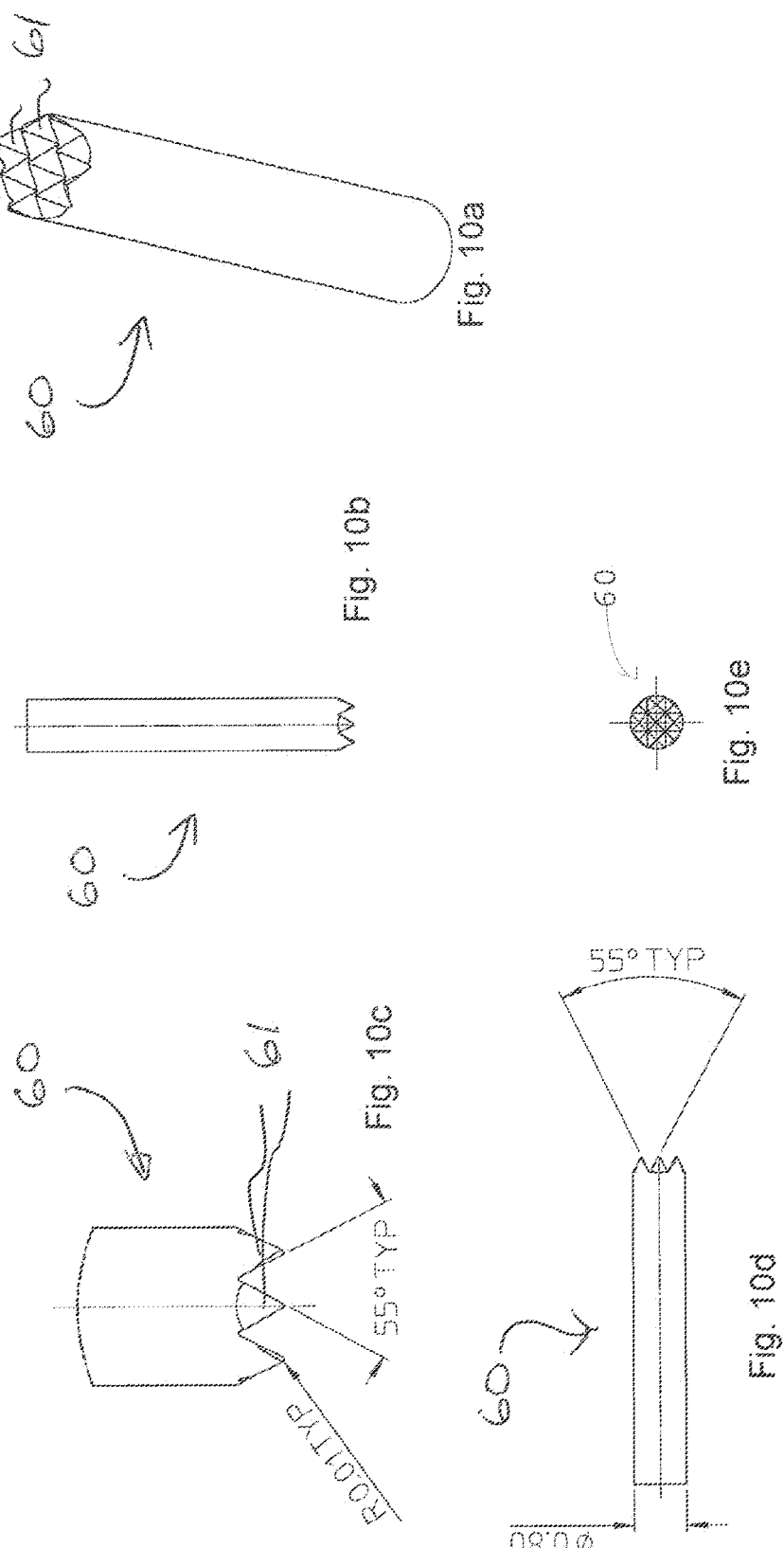
FIGS. 10a-10e illustrate an alternative spring pin according to the invention.

A vibrating multipoint contact pin head 50 as illustrated in FIG. 9 has the considerable advantage of being able to mechanically expose new areas for good electrical connection thus breaking down any oxidisation layers which can cause an insulation barrier. The multipoint contact pin increases the potential electrical contact surface area. The increased number of contact points, (which can vary in some embodiments from 7-14) act as a fail safe, if one contact becomes compromised the other contacts will form the required electrical contact. Additionally, the addition of the multi-points rather than a semi-hemispherical or flat contacting spring pin surface increases the specific force at these interfacial points, reducing the potential for undesirable fretting wear, and causing the multi-points to engage new micro surfaces. FIG. 10 shows another multi-point head 60 having seven points 61, with a V angle between of 55°, giving a point angle of 62.5°.

It has been found that a combination of the multi-point conducting pin and the film of cured adhesive provide particularly good reliability of contact. The points or tips penetrate the film to a greater extent than they would the underlying material of the (steel) support member 3. This allows an optimum combination, in which the steel of the support member provides excellent rigidity for supporting the apertured membrane 1 and the piezo 2, while at the same time the film part of the support member allows excellent electrical contact despite the harsh environment, in which the nebulizer may be operating for a prolonged period.

Furthermore, the retainer and sealing arrangement also contribute to the above features to help ensure reliable operation. The retainer 27 and O-ring 25 provide comprehensive and uniform support directly below the piezo 2, while the smaller-diameter O-ring 28 transmits support forces from above closer to the circumference of the membrane 1 where it is supported by the support member 3.

As the aperture plate 1 is attached to the support washer 3 by a thermal means such as by brazing, the elevated temperatures to effect a good joint bond can have an undesirable effect on any plating applied to the washer 3, which is typically Stainless Steel or Hastelloy. It is not possible to apply plating afterwards as it is difficult to mask off the aperture plate to prevent the ingress of conductive plating materials such as silver, gold, nickel or such like into the apertures.

One way of overcoming this is to apply a conductive adhesive similar to the adhesive 20 that bonds the piezo 2 to the support washer 3. This can be applied by automatic means as part of the process of application to attach the piezo 2. It is not required on top of the piezo 2 to maintain conductivity with the spring pin 10 as such elements are typically silver coated.

A particular current and voltage is required to drive the nebulizer 100 at the desired frequency to generate the optimum aerosol range [2.5-6.5 µm particle size and flow rates between 0.1 and 2 ml/min] Voltages are typically 12V and the nebulizer is driven at 128 kHz. The multi-pointed spring pin 50 makes excellent electrical contact with the piezo 2 and the washer 3, achieving a uniform performance in which an aerosol plume has the desired characteristics of particle size and flow rate.

Because the piezo is annular it ensures uniform radial vibration, which allows the core to work at its optimum mode of vibration. This symmetrical arrangement allows the aperture plate to move perpendicular to the piezo in a uniform and consistent manner, with a uniform forces applied around its circumference. Importantly, the pins do not interfere with the mode of vibration. Their springs act as dampeners which ensure that these electrical connectors do not impact on the core's natural frequency. They add additional mass through a normal reaction to the core's movement, this normal reaction being absorbed via the pogo pin spring.

Also, it will be appreciated that the arrangement of the invention only requires two holding posts. Because the pin 11 has conductive glue between itself and the main body of the support washer 3, fretting and resulting intermittency issues are avoided, and there is improved electrical connection. The use of a conductive glue reduces the potential of increased contact resistance which is a known indicator to electrical contact fatigue. Also, the use of multiple contact points 50 increases the potential electrical contact area.

The maintenance of electrical conductivity throughout the service life of the nebulizer is accomplished by the following features:

Pin contacting forces greater than L3N@2.1 mm deflection

Materials selected with low electrical resistivity

Less oxidising materials plated on to spring pin contacting surfaces

Spring pin head geometry selected so as to provide multipoint connecting points to the mating surface Spring head geometry selected so as to expose new surfaces to better electrical connection.

Also, it will be appreciated that the invention is used in the manufacture of aerosol generators which require electrical connection which have demanding requirements and which are required to be manufactured in high volumes without the use of laborious hand soldering.

The invention is not limited to the embodiments hereinbefore described, with reference to the accompanying drawings, which may be varied in construction and detail. For example, there may be a film of a material such as that of the film 20 on the piezo, for contact with the first conducting pin.

The invention claimed is:

1. An aerosol generator, comprising:
a first housing element defining a first cavity and a second cavity, the first cavity including a cylindrical portion, a frustoconical portion, and a first central axis;
a second housing element downstream of the first housing element, the second housing element defining a third cavity, the third cavity including a second central axis,
wherein the first central axis of the first cavity extends away from the second central axis of the third cavity at a non-zero angle, and
wherein the second cavity is laterally offset from the first cavity along a direction perpendicular to the second central axis;
a subassembly disposed between the first housing element and the second housing element, the subassembly including an annular member, a vibratable member, and an annular piezoelectric element;
a first electrically conductive pin at least partially disposed within the second cavity of the first housing element, the first electrically conductive pin extending parallel to the second central axis,
wherein the first electrically conductive pin is in physical contact with the subassembly and in electrical contact with the annular member; and
a second electrically conductive pin at least partially disposed within the second cavity of the first housing element, the second electrically conductive pin extending parallel to the second central axis,
wherein the second electrically conductive pin is in physical contact with the subassembly and in electrical contact with the annular piezoelectric element.

2. The aerosol generator of claim 1, wherein the frustoconical portion is downstream of the cylindrical portion.

3. The aerosol generator of claim 1, wherein the first cavity further includes an opening sealed by a sealing member.

4. The aerosol generator of claim 1, wherein the vibratable member is non-planar.

5. The aerosol generator of claim 1, wherein the first electrically conductive pin and the second electrically conductive pin are laterally offset in a radial direction with respect to the second central axis.

6. The aerosol generator of claim 1, wherein the subassembly includes an extension tab and wherein the first electrically conductive pin is in electrical contact with the annular member via the extension tab.

7. The aerosol generator of claim 1, wherein the annular piezoelectric element is bonded to the annular member via an adhesive and wherein an outer diameter of the annular member is greater than an outer diameter of the annular piezoelectric element.

8. An aerosol generator, comprising:
a first housing element defining a first cavity, the first cavity including a cylindrical portion, a frustoconical portion, and a first central axis;
a second housing element downstream of the first housing element, the second housing element defining a second cavity, the second cavity including a second central axis,
wherein the first central axis of the first cavity extends away from the second central axis of the second cavity at a non-zero angle;
a subassembly disposed between the first housing element and the second housing element, the subassembly including an annular member, a vibratable member, and an annular piezoelectric element;
a first annular seal at least partially disposed between the subassembly and the first housing element, the first annular seal including a first outer diameter;
a second annular seal at least partially disposed between the subassembly and the second housing element, the second annular seal including a second outer diameter that is larger than the first outer diameter of the first annular seal;
a first electrically conductive pin in electrical contact with the annular member; and
a second electrically conductive pin in electrical contact with the annular piezoelectric element,
wherein the first outer diameter of the first annular seal is radially inside of both the first electrically conductive pin and the second electrically conductive pin, and
wherein the second outer diameter of the second annular seal is radially outside of at least one of the first electrically conductive pin and the second electrically conductive pin.

9. The aerosol generator of claim 8, wherein the first annular seal and the second annular seal include different respective inner diameters.

10. The aerosol generator of claim 8, wherein both the annular member and the vibratable member are at least partially disposed between the first annular seal and the second annular seal.

11. The aerosol generator of claim 8, wherein both the annular member and the first housing element contact the first annular seal.

12. The aerosol generator of claim 8, wherein the first electrically conductive pin and the second electrically conductive pin are laterally offset and radially outside of the first annular seal in a radial direction with respect to a central axis of the second housing element and wherein the radially innermost electrically conductive pin is immediately adjacent the first annular seal.

13. An aerosol generator, comprising:
a first housing element defining a first cavity, the first cavity including a cylindrical portion, a frustoconical portion, a first central axis, and an opening sealed by a sealing member including a flap-type closure element,

a second housing element downstream of the first housing element, the second housing element defining a second cavity, the second cavity including a second central axis, wherein the first central axis of the first cavity extends away from the second central axis of the second cavity at a non-zero angle;

a subassembly disposed between the first housing element and the second housing element, the subassembly including an annular member, a vibratable member, and an annular piezoelectric element, wherein the subassembly includes an extension tab, and wherein the second housing element includes a slot configured to receive the extension tab;

a first electrically conductive pin at least partially disposed within the first housing element, the first electrically conductive pin in electrical contact with the annular member; and a second electrically conductive pin at least partially disposed within the first housing element, the second electrically conducive pin in electrical contact with the annular piezoelectric element.

14. The aerosol generator of claim 13, wherein the opening is included in an aperture positioned upstream of the cylindrical portion.

15. The aerosol generator of claim 14, wherein the flap-type closure element includes a projection extending into the aperture.

16. The aerosol generator of claim 14, wherein the aperture includes threading on an outer surface of the aperture.

17. The aerosol generator of claim 14, wherein the aperture is included in a cap enclosing the first cavity.

18. The aerosol generator of claim 13, wherein both the first electrically conductive pin and the second electrically conductive pin extend parallel to the second central axis.

19. The aerosol generator of claim 3, wherein the frusto-conical portion is downstream of the cylindrical portion and wherein the opening sealed by the sealing member is included in the cylindrical portion.

20. An aerosol generator, comprising:

a first housing element defining a first cavity, the first cavity including a cylindrical portion, a frustoconical portion, and a first central axis;

a second housing element downstream of the first housing element, the second housing element defining a second cavity, the second cavity including a second central axis, wherein the first central axis of the first cavity extends away from the second central axis of the second cavity at a non-zero angle;

a subassembly disposed between the first housing element and the second housing element, the subassembly including an annular member, a vibratable member, and an annular piezoelectric member;

a first annular seal disposed between the subassembly and the first housing element;

a second annular seal disposed between the subassembly and the second housing element;

a first electrically conductive pin in electrical contact with the annular member; and a second electrically conductive pin in electrical contact with the annular piezoelectric element, wherein the second housing element includes an annular platform extending radially inward and radially inside of an outer diameter of the annular piezoelectric element, the annular platform including an annular groove configured to at least partially receive the second annular seal.

* * * * *